United States Patent [19]

Liberti et al.

[11] Patent Number: 5,108,933

[45] Date of Patent: * Apr. 28, 1992

[54] MANIPULATION OF COLLOIDS FOR FACILITATING MAGNETIC SEPARATIONS

[75] Inventors: Paul A. Liberti, Churchville; Dhanesh I. Gohel, Philadelphia, both of Pa.

[73] Assignee: Immunicon Corporation, Huntingdon Valley, Pa.

[*] Notice: The portion of the term of this patent subsequent to Jan. 3, 2006 has been disclaimed.

[21] Appl. No.: 389,697

[22] Filed: Aug. 4, 1989

Related U.S. Application Data

[60] Continuation-in-part of Ser. No. 245,351, Sep. 16, 1988, which is a division of Ser. No. 906,521, Sep. 16, 1986, Pat. No. 4,795,698, which is a continuation-in-part of Ser. No. 784,863, Oct. 4, 1985, abandoned.

[51] Int. Cl.$^5$ ............... G01N 33/566; G01N 33/53; C12Q 1/00; C12Q 1/68
[52] U.S. Cl. .................................. 436/501; 435/4; 435/5; 435/6; 435/7.1; 435/971; 436/518; 436/524; 436/525; 436/526; 436/824; 436/528; 436/533; 436/534
[58] Field of Search ............ 435/4, 7, 4.6, 7.15, 435/971; 436/519, 520, 824, 526, 525, 501, 518, 524, 528, 533, 534

[56] References Cited

U.S. PATENT DOCUMENTS

| 3,970,518 | 7/1976 | Giaever . |
| 4,018,886 | 4/1977 | Giaever . |
| 4,230,685 | 10/1980 | Senyei et al. . |
| 4,267,234 | 5/1981 | Rembaum . |
| 4,267,235 | 5/1981 | Rembaum et al. . |
| 4,452,773 | 6/1984 | Molday . |
| 4,454,234 | 6/1984 | Czerlinski . |
| 4,552,812 | 11/1985 | Margel et al. . |
| 4,554,088 | 11/1985 | Whitehead et al. . |
| 4,659,678 | 4/1987 | Forrest et al. . |
| 4,795,698 | 1/1989 | Owen .................................... 435/7 |
| 4,920,061 | 4/1990 | Poynton et al. . |

FOREIGN PATENT DOCUMENTS 0230768 12/1986 European Pat. Off. .

OTHER PUBLICATIONS

R. R. Oder, IEEE Transactions on Magnetics, vol. MAG-12, No. 5, Sep. 1976.

Primary Examiner—Amelia Burgess Yarbrough
Assistant Examiner—David R. Preston
Attorney, Agent, or Firm—Dann, Dorfman, Herrell and Skillman

[57] ABSTRACT

Colloidal particles are converted into magnetic microagglomerates via manipulation of their colloidal properties, thereby facilitating their separation from solution.

60 Claims, No Drawings

MANIPULATION OF COLLOIDS FOR FACILITATING MAGNETIC SEPARATIONS

This application is a continuation-in-part of copending U.S. patent application Ser. No. 245,351, filed Sep. 16, 1988, which, in turn, is a division of U.S. patent application Ser. No. 906,521, filed Sep. 16, 1986, now U.S. Pat. No. 4,795,698, which, in turn, is a continuation-in-part of U.S. patent application Ser. No. 784,863, filed Oct. 4, 1985, now abandoned.

BACKGROUND OF THE INVENTION

The present invention relates to improvements in magnetic separation methodology, having particular utility in various laboratory and clinical procedures involving biospecific affinity reactions. Such reactions are commonly employed in testing biological samples for the determination of a wide range of target substances, including antigens, specific antibodies, specific biological factors such as vitamins, cell subpopulations (both eucaryotic and procaryotic), cell components, viruses and specific nucleic acid sequences, as in the case of gene probe analysis.

As used herein, the term "target substance" refers to any member of a specific binding pair, i.e., a pair of substances exhibiting a mutual affinity of interaction, and includes biospecific ligands and receptors. "Ligand" is used herein to refer to substances, such as antigens, haptens and various cell-associated structures, having at least one characteristic determinant or epitope which is capable of being biospecifically recognized by and bound to a receptor. "Receptor" is used herein to refer to any substance or group of substances having a biospecific binding affinity for a given ligand, to the exclusion of other substances. Among the receptors determinable via biospecific affinity reactions are antibodies (both polyclonal and monclonal), antibody fragments, and nucleic acids. The determination of any member of a biospecific binding pair is dependent upon its selective interaction with the other member of the pair.

The term "antigen", as used herein, refers to any substance to which antibodies can be produced, and includes haptens which can be made immunogenic by means known to those skilled in the art. The term "specific antibodies" is used herein to refer to antibodies produced in response to a specific stimulation of the host, be that stimulation due to specific exogenous agents, e.g., germ entities or specific inoculation, or stimulation resulting from endogenous components. Many biologically relevant target substances other than antigens and specific antibodies can be recognized via biospecific affinity reactions, e.g., the members of specific binding pairs such as Vitamin B-12/intrinsic factor. "Gene probes" include all pairs of complementary nucleic acid sequences which can undergo stable hybridization reactions, such pairs resulting from naturally occurring complementary base pair reactions or from reactions involving appropriately synthesized complementary oligonucleotides. Cells, e.g. erythrocytes or leukocytes, microorganisims, e.g. bacteria, and viruses are also separable from a mixed population thereof, by reason of their interaction with specific receptors, in accordance with the present invention.

Various methods are available for determining all of the above-mentioned target substances based upon complex formation between the substance of interest and its specific binding partner. Means are provided in each instance whereby the level of target substance/binding partner complex formation is detectable.

In the case of a competitive immunoassay to determine antigen, for example, the antigen of interest in a test sample competes with a known quantity of labelled antigen for a limited quantity of specific antibody binding sites. Thus, after an appropriate reaction period the amount of labeled antigen bound to specific antibody is inversely proportional to the quantity of antigen in the test sample. Competitive assays for antibodies, employing labeled antibodies (typically monoclonal antibodies) rather than labeled antigen, function in an analogous manner. In contrast, immunometric assays, commonly known as "sandwich" assays, involve the formation of a sandwich whose "layers" are: antibody/multivalent (minimally bivalent) antigen/antibody. When one of the antibodies is labeled, the amount of labeled antibody which is bound for each complete sandwich complex (antibody/antigen/antibody) is directly proportional to the amount of target antigenic substance present in the test sample. Sandwich assays can be performed in multistep fashion with polyclonal antibodies or in fewer steps when monoclonals directed to independent antigenic determinants are employed. In both of the foregoing immunoassay techniques quantitation requires a physical separation of bound from free labeled ligand or labeled receptor. Such assays are known as heterogeneous assays.

In the case of non-antigen/antibody biospecific binding pairs, such as the determination of Vitamin B12 with its biospecific binding partner, intrinsic factor, a test sample being assayed for the presence of the vitamin is contacted with a known amount of the same vitamin bearing a suitable label and a limited quantity of intrinsic factor. Cobalt is commonly used as the label in such assays. Just as in the case of the competitive immunoassay technique described above, the amount of label bound to intrinsic factor is inversely proportional to the amount of vitamin in the sample. In such an assay bound/free separation must be performed for purposes of quantitation.

For gene probe analysis, a competitive assay format may be employed which is analogous to the above described competitive immunoassay techniques. A sandwich type assay, such as that described above, may also be employed. Again, separation of bound label from unbound label in the test sample is required for quantitation.

The same basic approach involving bound/free separation is routinely used in cell separation techniques.

Various methods have been reported for performing bound/free separations in heterogeneous systems in order to determine the bound/free ratio of labeled ligand or receptor. These may be classified for purposes of this discussion into liquid phase and solid phase techniques. Liquid phase separation techniques include (1) adsorption of free ligand onto materials which may be filtered or centrifuged, such as cellulose powder, dextan-coated charcoal, Kaolin, and the like, where a differential adsorption of ligand vs. receptor is possible; (2) non-specific or specific precipitation of antibody or receptor; (3) chromatographic separation based on molecular size; and (4) electrophoresis based on mobilities of components of the test sample; see, for example, *Methods of Investigative and Diagnostic Endocrinology, Part I*, pp. 84-120, S. Berson et al. eds., American Elsevier, N.Y. (1973).

One of the liquid phase separation techniques commonly employed involves the use of second antibodies. As an example, a competitive immunoassay may be performed by employing rabbit antibodies reacting with an appropriately labeled antigenic substance corresponding to the target substance of interest. After an appropriate incubation period, labeled antigen bound specifically to the rabbit antibodies can be determined by removing the rabbit antibodies from solution. Antibody removal can be achieved by forming a specific precipitate using second antibodies that immunospecifically interact with the rabbit antibodies. Thus, by adding an appropriate quantity of goat anti-rabbit IgG, for example, the rabbit IgG antibodies in the fluid phase are removed from solution and bring with them specifically bound labeled antigen. With appropriate washing of the resultant precipitate the quantity of labeled antigen bound to the rabbit antibodies can be quantitatively determined.

The Farr method, involving ammonium sulphate (($NH_4)_2SO_4$) precipitation of low molecular weight, hapten-like, labeled antigens, typifies the non-specific liquid phase separation methodology. R. Farr, *J. Infect. Dis.*, 103:239 (1958). The Farr method is performed by adding a sufficient quantity of ammonium sulphate to the reacted test sample to cause precipitation of the bound antibodies therein, leaving behind the unbound labeled antigen. In employing the Farr method, as well as certain other liquid phase separation techniques, e.g., those involving precipitation with alcohol, dioxane and polyethylene glycol, it is important that the labeled antigen be unaffected by ammonium sulphate, or other protein precipitation agent.

The above-mentioned second antibody technique has been improved by the addition of promoters, e.g., polyethylene glycol, to the test sample to promote precipitation of lesser quantities of specific antibody/second antibody precipitates. The crosslinking of antibodies to facilitate phase separation can be done either before or after equilibration with the labeled antigen. In the former case, the cross-linked or aggregated antibody is a convenient reagent. Reagent so used ceases to fit the liquid phase separation classification, however, as not all reagents are in solution at the start of the assay.

The foregoing assays employing liquid phase separation techniques involve transforming a soluble biospecific binding partner to a precipitate that results either from crosslinking via non-covalent bonding or from the conversion of macromolecules, which exist in a colloidal state, to an insoluble form. Such conversions via "salting out" or the use of "non-solvent" proceed via well known colloidal properties of the macromolecules involved. See, A. Alexander et al., *Colloid Science*, Volumes 1 and 2, Oxford Press, London, (1949).

More recently, assays involving biospecific binding pairs have utilized solid phase separation techniques. Probably the simplest approach in solid phase separation consists of coating the interior surface of a suitable vessel with one member of the biospecific binding pair of interest, thus creating a stationary solid phase device. Methods for absorption or covalent attachment of the required reagents to such surfaces are well known to those skilled in the art. Solid supports may also comprise surfaces which can be emersed into a test medium. Phase separation simply entails removing the medium from contact with the surface after sufficient time has elapsed for biospecific interaction to occur between the binding pair members.

Among the more commonly used solid phase separation techniques are those employing finely divided inert particles (charcoal, derrivatized glass, cross-linked carbohydrate and/or polymer particles, as well as beads, e.g. latex), or even cross-linked insolubilized antibodies. Such particles or beads may be used to adsorb unbound materials directly, or through appropriate processing, may be used to create a solid phase bearing the appropriate binding partner. Bound/free separations may be accomplished gravitationally, e.g., by settling, or, alternatively, by centrifugation of the finely divided particles or beads from solution. If desired, such particles or beads may be made magnetic to facilitate the bound/free separation step. Magnetic particles are well known in the art, as is their use in immuno-and other biospecific affinity reactions. See, U.S. Pat. No. 4,554,088 and *Immunoassays for Clinical Chemistry*, pp. 147–162, Hunter et al. eds., Churchill Livingston, Edinborough (1983). Generally, any material which facilitates magnetic or gravitational separation may be employed as a solid support. Solid phase materials which are particulate and free to move in solution, such as those described above, are known as mobile solid phase reagents.

Small magnetic particles have proved to be quite satisfactory as a mobile solid-phase, as they provide very high surface areas, give reasonable reaction kinetics and can readily be removed from solution by means of commercially available magnetic devices (Ciba-Corning Medical Diagnostics, Wampole, Mass.; Serono Diagnostics, Norwell, Mass.). Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Several of these particles are useful solid supports, having reasonably good suspension characteristics when mildly agitated. Insofar as is known, however, absent some degree of agitation, all of the magnetic particles presently in commercial use settle in time and must be resuspended prior to use. This adds another step to any process employing such reagents.

Small magnetic particles, such as those mentioned above, generally fall into two broad categories. The first category includes particles that are permanently magnetized; and the second comprises particles that become magnetic only when subjected to a magnetic field. The latter are referred to herein as magnetically responsive particles. Materials displaying magnetically responsive behavior are sometimes described as superparamagnetic. However, certain ferromagnetic materials, e.g., magnetic iron oxide, fall into the magnetically responsive category when the crystal is about 300 A or less in diameter. Larger crystals of ferromagnetic materials, by contrast, retain permanent magnet characteristics after exposure to a magnetic field and tend to aggregate thereafter. See P. Robinson et al., *Biotech Bioeng.* XV:603–06 (1973).

Magnetically responsive colloidal magnetite is known. See U.S. Pat. No. 4,452,773 and published International Application PCT WO 87/02063. Magnetically responsive materials that behave as true colloids are characterized by their stability to gravitational separation from solution for extended periods of time and their sub-micron particle size, which is generally less than about 200 nanometers (0.20 microns). Such materials are believed to be composed of a crystalline core of superparamagnetic material surrounded by molecules, which may be physically absorbed or covalently attached, and which confer stabilizing colloidal properties. It is further believed that such colloidal materials are so small that they do not contain a complete magnetic domain and that their Brownian energy exceeds their magnetic moment. As a consequence, North Pole, South Pole alignment and subsequent mutual attraction/repulsion of these colloidal materials does not appear to occur even in moderately strong magnetic fields, contributing to their solution stability. Accordingly, colloidal magnetic materials are not readily separable from solution as such, even with powerful electromagnetics but, instead, require gradient field separation techniques. See, R. R. Oder, *IEEE Trans. Magnetics,* 12:428-35 (1976); C. Owen and P. Liberti, *Cell Separation: Methods and Selected Applications,* Vol. 5, Pretlow and Pretlow eds., Academic Press, N.Y., (1986). The gradient fields normally used to filter such materials generate huge magnetic forces.

Solid phase systems in which a member of a specific binding pair, or a reagent which will bind one member of the pair, is immobilized not only facilitate phase separation, but permit separation to be accomplished simply and rapidly. See, for example, U.S. Pat. No. 4,271,140. The speed with which such separations can be performed is vital in the case of biospecific affinity reactions, as significant re-equilibration of the biospecific binding pair members may take place given sufficient time. Theoretically, antibody interacting with low molecular weight labeled antigen and test antigen could be separated from solution by ultracentrifugation but the time factor and difficulty of such a process would be impractical. For similar reasons, electrophoretic and chromatographic means for such separations are not often used.

The aforementioned U.S. Pat. Nos. 3,970,518 and 4,018,886 to Giaever relate to biological separations using protein-coated small magnetic particles. These patents describe an apparatus and separation method utilizing magnetic particles, ranging in size from colloidal to 10 microns, coated directly with antibody that interacts specifically with the biological entities of interest. However, the above-noted U.S. Pat. No. 4,230,685 to Sengei et al., which discloses the preparation of magnetic particles and their use in cell and other separations, refers to the disclosure of U.S. Pat. No. 3,970,518 and states that there is no literature verification that uncoated magnetic particles may effectively be made to bind directly with antibody. Moreover, the above-noted U.S. Pat. No. 4,554,088 to Whitehead et al., which relates to chemical coupling of antibodies to silanated metal oxide magnetic particles, states that antibodies absorbed on iron oxides are substantially detached by 24 hour incubation at 50° C. in 1M sodium chloride. Furthermore, with respect to superparamagnetic, resuspendable colloidal particles (such as those used in the practice of the present invention), the method of absorption of antibodies proposed in U.S. Pat. Nos. 3,970,518 and 4,018,886 could not easily be made to work on such particles, as the field strength required to capture the particles for washing or subsequent retrieval would be enormous and cannot be achieved with the device proposed. Insofar as is known, apart from the aforementioned colloidal magnetite preparations, there is no currently available way of coating superparamagnetic, resuspendable colloidal particles of iron oxide so as to form a suspensoid, with the dispersed particles having cores of single iron oxide crystals.

As should be apparent from the foregoing, the need for performing bound/free separations is essential to achieving accurate determination of specific target substances. Among the various prior art assays mentioned above, techniques involving second antibody precipitation provide a notable advantage in that reaction of first antibody with labeled and unlabeled analyte proceed with diffusion controlled kinetics. The addition of second antibody reagents or insolubilizing agents in certain instances to cause precipitation, although cumbersome, affords an efficient way of converting soluble macromolecules to an insolubilized state. The introduction of immunological reagents on solid supports results in simplicity of operation, but with markedly slower reaction rates. As an example, coated tube technology requires significantly longer incubation periods and requires constant agitation of the test vessel. Although, mobile solid-phase reagents markedly increase available surface area for reaction and consequently shorten reaction time, such reagents also typically require agitation to maintain a uniform suspension.

In view of the decided advantages afforded by magnetic separations in the assays described above, which include ease of separation, safety (eliminating possible container breakage during centrifugation) and the avoidance of energy-consuming devices to serve as magnetic field sources, a reagent capable of facilitating bound-free separation that normally remains in solution, reacts with the reaction kinetics of macromolecules or colloids and is readily agglomerable would be ideal, particularly if such material were magnetic or could be rendered magnetic, so as to be more easily removable from solution.

SUMMARY OF THE INVENTION

In accordance with the present invention, we have devised a method whereby particles which are at once colloidal and magnetically responsive can be used effectively for the separation of any one of a variety of target substances from a test medium suspected of containing the substance of interest through conversion of the particles to micro-agglomerates including the target substance, via manipulation of their colloidal properties. The resultant agglomerates can subsequently be removed from the medium using ordinary laboratory magnets, as the particles are comprised of sufficient magnetic material, above an empirical threshold, to effect such removal. The method of the invention is carried out simply by adding to the test medium agglomerable and resuspendable colloidal particles, which are capable of stable suspension in the test medium, forming a magnetic agglomerate comprising the colloidal particles and any target substance present in the test medium and separating the resulting magnetic agglomerate from the medium.

According to one preferred embodiment of the invention, colloidal, magnetic particles comprising a specific binding substance for the target substance are used in performing the method, so that the product of the interaction between these two substances is associated with the magnetic particles as it is formed. In another preferred embodiment, appropriate specific binding substances are added to the test medium to interact with the target substance in the manner of a two-site immunometric assay, with protein colloidal magnetic particles being added to the test medium to render the product magnetic. In this particular embodiment, the added protein colloidal magnetic particles comprise a specific binding moiety having binding affinity for one of the specific binding substances used to interact with the target substance. It is also within the scope of the present invention to effect separation of a target substance from solution through binding to agglomerable, resuspendable colloidal particles, which are themselves nonmagnetic, with magnetic conversion occurring through addition to the test medium of a magnetic colloid, e.g. polymer/protein colloidal magnetite. In this latter embodiment, the product of the interaction between the specific binding substance and the target substance is rendered magnetic, not because one member of the binding pair is affixed to a magnetic support, but rather because of charge-charge interaction between the two colloidal materials.

The method of the invention is particularly useful for performing bound/free separations in qualitative and quantitative analyses involving biospecific affinity reactions. Although the magnetic agglomerate formed in carrying out the method of the invention is most easily and conveniently separated by applying a magnetic field to the liquid medium, agglomerate separation may be accomplished by other means, including, e.g., centrifugation or filtration, if desired. In addition to enabling the detection and/or determination of low molecular weight and macromolecular weight analytes, the method of the invention has considerably broader potential applications in analysis of cell mixtures, or samples suspected of bacterial or other microorganism contamination. In addition to facilitating bound/free separations in the detection and/or determination of cells, bacteria or other microorganisms, the method of the invention may also be useful in the concentration of such materials from various sources in conjunction with, or apart from any specific analytical or diagnostic technique.

The conversion of colloidal materials for use in separation methods according to one embodiment of this invention, which will be described in detail below, is properly classifiable with the liquid phase separation techniques described above. By analogy to molecular antibody, colloidal magnetically responsive particles, containing antibody or some other specific binding substance, whether receptor or ligand, can be made to interact with the target substance of interest to yield magnetically attractable agglomerate, either by non-specific or specific means. Non-specific means includes the use of various known agglomerating agents, such as counterion, solvent or second colloid addition, whereas specific means includes the use of agglomerating agents comprising appropriate cross-linking agents, e.g. multivalent biospecific reagents.

When magnetic particles comprising specific binding substance for the target substance are used in performing the method of the invention, agglomeration may occur as a result of cross-links formed between the target substance and specific binding substance upon incubation, depending on the concentration of the target substance in the test medium, the nature of the specific binding substance and other factors. The same is true where the method of the invention is practiced using colloidal, magnetic particles comprising a specific binding moiety, having binding affinity for binding substance that interacts specifically with the target substance. If cross-linking does not occur due to specific means, non-specific agglomerating agents, which may comprise magnetic material, as noted above, are added to promote agglomerate formation.

In carrying out the present invention, a reagent is prepared for the target substance of interest, which reagent preferably comprises a biospecific binding material having binding affinity for the target substance, and a colloidal, magnetically responsive particle. The magnetic properties of the particle are such that the reagent is capable of stable suspension in a test medium for prolonged periods, and, absent the addition of a suitable agglomerating agent, will remain suspended even when exposed to an external magnetic field. The reagent and the target substance react with nearly diffusion-controlled reaction kinetics and the resulting product can be removed from solution by flocculation with appropriate crosslinking reagents, or the other well known non-specific means referred to above for causing controllable agglomerate formation. Such agglomerates can readily be separated using ordinary laboratory magnetic devices, such as those produced by Corning or Serono (1–3 k Oersteads). The resulting agglomerates may also be removed from the test medium by centrifugation or filtration.

Other advantages of the colloidal assay of the invention result not only from rapidity of reaction, as noted above, but from surface area considerations and sequelae. For example, assuming sphericity, the colloidal particles used in practicing this invention have about 90 square meters per gram of material and, of course, this is area to which various specific binding substance can be bound and which are subsequently available for reaction. In the examples set forth below, an amount of colloidal magnetite corresponding to 70–150 $cm^2$ of surface area per assay is most times optimally employed. By comparison, assays performed using conventional mobile solid phases, e.g., coated beads (typically 0.25 inch diameter bead) or stationary solid phase devices, e.g., coated tubes, have about 1.3–1.5 $cm^2$ of surface area available for reaction with a binding partner. It is likely that David et al., U.S. Pat. No. 4,376,110, took this factor into account (Wang et al., Clin. Chem., 27:1063, Abs. No. 197, (1981)) in determining that assays which are performed with area-limited binding surfaces, and which use a pair of monoclonal antibodies, require antibodies having affinities of $10^8$ or greater, in order for such assays to function in detecting levels of analytes normally found in physiological samples. The surface area provided by colloidal reagents used in practicing this invention, on the other hand, decreases that affinity requirement by between one and two orders of magnitude. Thus, assay conditions known to have generally negative effects on antibody affinity, such as high concentration of specific salt, high ionic strength or acidic pH may be employed where the functional affinity is considerably less than $10^8$. In many assays such conditions are required to reduce non-specific binding and also may be used to significantly reduce antibody - Complement system interactions. See for example, Burton et al. Nature, 288:338–44 (1980); Easterbrook-Smith et al. Biochem. Soc. Trans., 6:1126–31 (1978). It is noted in passing that the $10^8$ affinity requirement determined by David et al. in U.S. Pat. No. 4,376,110 need not apply when mixtures of monoclonals (i.e., more than 2) are employed to perform immunometric assays. This is so because of the well known enhancement and synergy of affinities which results upon mixing of specific monoclonals. See, Ehrlich et al., J. Immunol. 128:2709 (1982).

Other operational advantages are realized when using colloidal particles composed, at least in part, of magnetic material. The ability to convert colloidal particles into magnetically attractable agglomerates can be used to particular advantage where conversion is effected by crosslinking of the members of specific binding pairs. Such conversion ("non magnetic" to "magnetic") serves as a read-out of the cross-linking reaction, as the reaction product, which cannot be separated from solution using ordinary magnetic fields, is converted into an agglomerate which can be so separated. In performing the assay of the invention using colloidal magnetically responsive particles, agglomerate formation causes the concentration of significant magnetic material above some emperically determinable threshold value. Such conversion, which is promoted by the attachment of multi-valent, i.e. at least bivalent, binding partners to appropriate colloidal particles, can be inhibited by specific monovalent analytes. The occurrence or non-occurrence of the resulting agglomerate at the pole of a magnet affords a readily visualized read-out of such reactions.

DETAILED DESCRIPTION

The methods of the invention involve the conversion of colloidal magnetic particles, through microgglomeration to a form which is readily separated from solution using conventional laboratory magnets.

As used herein, the terms "microagglomeration" or "agglomeration" include, among other phenomena, the coherence of colloid particles resulting from what is believed to be a collapse, in whole or in part, of the particles' ion clouds by appropriate counterions. In the colloid literature this phenomenon is commonly termed coagulation. A related phenomenon alluded to above and which will also be described further hereinbelow is particle coherence caused by cross-linking between the members of a specific binding pair. Such coherence by specific crosslinking of particles is generally referred to in the colloid literature as flocculation. See, e.g., V. LeMer, *Faraday Disc.*, 42:248 (1966). The term "separate" is used herein in a broad sense, which includes isolating or segregating an agglomerate in solution, e.g. along the side of a vessel under the influence of an externally applied magnetic field, as well as actually removing agglomerate from solution.

Among the characteristic properties of the colloidal, magnetic particles used in the practice of this invention are their ability to remain in stable suspension, their agglomerability and their resuspendability. The expression "stable suspension", as used herein, refers to a suspension in which the finely divided, undissolved magnetic particles are uniformly dispersed throughout a compatible liquid medium and do not settle or otherwise agglomerate, in the absence of an added agglomerating agent, when left quiescent at standard temperature and pressure for up to two days. The colloidal, magnetic particles described herein remain in stable suspension even if subjected to magnetic forces the source of which is only external to the test medium. It should be understood, however, that even when unagglomerated, these colloidal magnetic particles are susceptible to separation from the test medium by conventional high gradient magnetic separation techniques, wherein separation is effected by generating substantial magnetic forces originating within the medium from which the particles are to be separated. The term "agglomerable", as used herein, refers to the ability of the above described colloidal magnetic particles to gather or collect into a mass or cluster under the influence of an agglomerating agent; and the term "resuspendable" refers to the particles' capability of being redispersed, after agglomeration, e.g., by coaggulation or flocculation, to yield a stable suspension.

Suitable colloidal systems that may be used in the practice of this invention range from those in which each particle is a crystalite containing a great many identical atoms, to those in which the colloidal particle is believed, in most instances, to consist of a single molecule, or complex mixtures of several molecules which comprise single particles. In 1905, Perrin introduced the terms hydrophilic and hydrophobic to differentiate between two classes of aqueous suspension. In hydrophilic suspensions, the disperse phase has high affinity for the aqueous medium, whereas the disperse phase in a hydrophobic suspension has a low affinity for the aqueous medium. These original terms were later replaced by the more generalized terms lyophilic and lyophobic, respectively. Most proteins are lyophilic in an aqueous dispersion medium, whereas metal sols are lyophobic. Additionally, lyophilic colloids are more stable to electrolyte, requiring relatively high salt concentrations to be "salted out", while lyophobic colloids are easily precipitated by electrolyte. Generally, lyophilic colloid solutions are thermodynamically stable, single-phase systems, whereas lyophobic suspensions are not.

The disperse phase of the colloidal systems described herein includes a binding substance, e.g. receptor, ligand or some other biospecific binding material, which together with the target substance constitute a specific binding pair. Typically such materials include metal sols, latex particles, magnetite particles and other such colloids to which one member of a specific binding pair can be attached, either covalently or by adsorption. For example, the use of antibody or antigen adsorbed to colloidal gold is well known in performing agglutination reactions. Biospecific binding materials may be directly adsorbed on latex and certain magnetites or covalently linked with derivatized latex. Cyanogen bromide activation is a convenient way for covalently coupling colloidal dextran magnetite to substances having free amines. See, for example, U.S. Pat. No. 4,452,773. Covalent attachment of biospecific binding material to dextran magnetite may similarly be accomplished via other functional groups, according to procedures well known to those skilled in the art.

A preferred colloidal, magnetically responsive material which has been used effectively in performing assays involving biospecific affinity reactions, as exemplified below, is polymer/protein magnetite. Such materials are prepared by the coprecipitation of suitable polymers or proteins with ferrous and ferric chloride salts. Coprecipitation is conveniently accomplished by addition of base. When the addition of base is carried out under rigorously controlled conditions, protein and other bio-polymers, such as monoclonal antibodies, enzymes, viral antigens, complement components, wheat germ agglutinin, and nucleic acids, can be incorporated onto colloidal, magnetically responsive particles and retain native biological activity. A detailed description of this methodology is set forth in U.S. patent application Ser. No. 906,521, filed Sep. 16, 1986, now U.S. Pat. No. 4,795,698, which was a continuation-in-part of Ser. No. 784,863, filed Oct. 4, 1985, and now abandoned. The complete disclosures of Ser. No. 906,521 and 784,863 are incorporated by reference in the present specification, as if set forth herein in full.

From electron microscopy studies of this colloidal protein magnetite, the particles appear to have dense cores, (presumably magnetite), surrounded by a less dense region (presumably protein).

Colloidal polymer or protein magnetite can be prepared with highly controllable, polymer/protein magnetite ratios. Typically, the particles are precipitated from solutions of hydrated ferric and ferrous chlorides at 3.5 and 1.5 mg/ml, respectively, with protein content ranging from 500 ug/ml to 1.5 mg/ml. After appropriate washing, resuspension and sonication of such precipitates, colloidal, magnetically responsive particles are produced, wherein the mean diameter of particles is approximately inversely proportional to starting protein concentration. Particles about 20 nanometers or less in diameter are obtained at the higher protein concentrations, whereas particles approximately 100 nanometers in diameter are obtained at the lower end of the range of protein concentrations noted above. It has been found that the ease with which various of these colloidal solutions can be salted out is inversely related to the protein concentration of the solution and is directly related to particle size. In other words, the smaller, higher protein containing particles are more difficult to salt out. These results suggest that the particles having higher protein concentration are more lyophilic, which would be expected because of the greater interaction between solvent water and protein, as compared with magnetite. Other possible explanations for this observed phenomenon are that the magnetic cores of the larger colloidal particles may be easier to flocculate because of their magnetic moments, or that the smaller particles offer relatively larger surface area and consequently more surface charge to be neutralized. In the case of protein adsorption onto colloidal gold, an analogous phenomenon occurs, i.e., the conversion of colloidal gold from a lyophobic to a lyophilic colloid. In 1857 Faraday observed the protective effect of gelatin on color changes (flocculation) promoted by salt. Later, in 1898, Zsigmondy showed in a quantitative sense that the coagulation of colloidal gold by sodium chloride could be prevented by adsorbed protein. Thus, adsorbed protein can be thought of as acting to convert lyophobic colloidal gold to a more lyophilic material.

In a particularly preferred embodiment of this invention colloidal, magnetically responsive particles bearing (i) a biospecific binding material having binding affinity for the target substance of interest or (ii) a suitable retrieval agent, for example, anti-fluorescein, where a fluoresceinated receptor for the target substance is used, are incubated with an appropriately labeled specific binding substance and test sample suspected of containing the target substance, under conditions such that agglomeration of such particles does not occur. Agglomeration may not occur, for instance, because the binding capacity of the specific binding substance or the concentration of the target substance in the test medium is too low. At an appropriate time, following the binding of sufficient labeled substance (or inhibition thereof), an agglomerating agent, which may be either non-specific, or specific preferably the former, e.g., a simple salt solution, is added to the incubation mixture to cause agglomeration. Agglomeration may be brought about by the addition of a second non-specific agglomerating agent, e.g., an appropriately chosen colloid, if desired.

As colloidal protein magnetite is an anionic colloid, it would generally be expected that cationic colloids could be used to promote coagulation. It has been found in practice, however, that opposite charge-induced coagulation does not always occur. Clq, which is a 400,00 dalton euglobulin of the Compliment system, having a pI>9.0 and substantial positive charge at neutral pH, is an example of a naturally-occurring cationic colloid which can coagulate protein magnetite. The ability of Clq to coagulate protein magnetite is independent of Clq's functional binding to antibody Fc, as it has been found that, even when devoid of biological activity, Clq will coagulate antibody colloidal magnetite, as well as BSA colloidal magnetite. Numerous other natural or formulated, charged colloids, including, by way of example hydrates of iron and aluminum, methyl violet methylene blue, and the like, may be useful for this purpose, as well.

Alternatively, agglomeration may be effected by means of a specific agglomerating agent capable of cross-linking a component of the colloidal magnetic particles, such as specific antibody. Similarly, the well-studied interaction of biotin with avidin may be used to advantage for purposes of causing specific agglomeration reactions where such agents are not otherwise participating in the method. Under such conditions, the resulting agglomerate may be removed from solution via centrifugation, filtration or, preferably via magnetic separation. It is also possible to use the above-described non-specific and/or specific agglomerating agents in various combinations, if desired. Thus, second colloid addition plus salting out would be feasible, as would the use of a second magnetically responsive colloidal particle bearing a receptor capable of cross-linking with a substance present on the colloidal protein magnetite initially added to the test sample.

Another useful application of the conversion of colloidal material to a magnetically separable form by the addition of a second colloid, is to use protein colloidal magnetite as the agglomerating agent for some other non-magnetic colloidal material, where the latter bears the target substance of interest. A variation of the same concept is to bind colloidal protein magnetite to a second non-magnetic colloid via a biospecific affinity reaction, such as goat anti-rabbit IgG colloidal magnetite binding to rabbit antibodies on some other colloid, e.g., latex, when such rabbit antibodies or some other antibodies on the latex are specific for the target substance of interest. This approach enables magnetic separation of latex from solution.

Colloidal reagents and non-specific or specific agglomerating agents may be added to the test medium simultaneously, rather than sequentially, as previously described. This can be accomplished by adding a suitable agglomerating agent to one of the colloidal reagents used in the assay, so that conversion of the colloid takes place after a substantial level of ligand/receptor interaction has occurred. For example, in a competitive immunoassay, a labeled receptor solution might be prepared with an appropriate agglomerating agent therein. That preparation, when added to a test sample containing a suitable colloidal material bearing a biospecific binding substance having binding affinity for the ligand of interest, would provide the labeled receptor reactant of the competitive biospecific affinity reaction, as well as the colloid conversion agent. Theoretically, it is possible to have the colloidal conversion take place after a substantial level of ligand/receptor interaction has occurred, because of the complexity of the kinetics of the former relative to those of the latter. Most ligand- /receptor interactions are diffusion controlled processes, whereby the extent of reaction decreases in each succeeding time interval. On the other hand, the conversion of colloidal material to an agglomerate which can be separated from solution, and which, in the case of magnetic colloids, is an agglomerate of substantial size, is kinetically a complex process involving many particles. Further, from experiments described below it appears that an agglomerate must achieve a critical size before becoming magnetically separable from solution. For relatively mono-dispersed magnetic colloidal particles, it has been found that an appropriate sized agglomerate may require from 30 to 90 minutes of reaction or formation time, depending on the quantity of agglomerating agent employed. By optimal timing of the critical point of the colloidal conversion to allow for a sufficient quantity of ligand/receptor interaction to have taken place, quantitation of the assay result is possible.

As can be seen from the foregoing, the manipulation of colloidal particles to which appropriate biospecific binding materials have been affixed, allows bound/free separations to be performed by means and/or under conditions not heretofore possible. Application of such concepts to analytical measurements involving a variety of biospecific binding pairs should be self-evident to those skilled in the art. These concepts may also be applicable to separations for industrial use, for example, the large scale purification of biologically active molecules by appropriate receptors.

The following examples are provided to describe the invention in further detail. These examples, which set forth the best mode presently contemplated for performing the assay of this invention, are intended to be illustrative only, and should not be construed as restricting in any way the scope of application of the invention.

EXAMPLE I

Colloidal Protein Magnetite

Preparations of colloidal protein magnetite were made comprising, as the protein component, goat anti-mouse IgG (Fc specific), rabbit anti-fluorescein, mouse monoclonal anti-human chorionic gonadotropin (HCG), mouse monoclonal anti-progesterone, and bovine serum albumin (BSA). Goat anti-mouse IgA (Fc specific) was obtained from Jackson Laboratories, West Grove, Pa., rabbit anti-fluorescein from East Acres Biologicals, Southbridge, Mass., mouse monoclonal anti-HCG from Cambridge Medical Diagnostics, Billerica, Mass., mouse monoclonal anti-progesterone from Scantibodies, Santee, Calif., and BSA from Sigma Chemical Co., St. Louis, Mo. Preparations were prepared at either 0.50, 0.75 or 1.0 mg/ml total final protein concentration. Protein solutions (2×concentrations) were mixed with equal amounts of 2×iron chloride solutions to obtain desired final protein concentration. For the goat anti-mouse Fc and rabbit anti-fluorescein, antisera were first absorbed on sepharose columns to which had been covalently coupled human serum proteins via standard cyanogen bromide coupling methodology. After adsorption, antisera were diluted with BSA to give a 2×protein concentration containing serum proteins at 0.5 mg/ml. For the monoclonal antibody-colloidal magnetite preparations, appropriate concentrations of monoclonal antibody (5 or 10 ug/ml) were mixed with BSA at either 1.0, 1.5 or 2.0 mg/ml.

To form a colloidal protein magnetite preparation, one of the former 2×protein concentration solutions was mixed with an equal quantity of aqueous solution of $FeCl_3.6H_2O$ and $FeCl_2.4H_2O$, at 7.0 and 3.0 mg/ml respectively. Ammonium hydroxide (3.75-4.0%) or 2.0M $NH_4Cl$ buffer pH 9.5 was added to well-stirred protein-aqueous iron salts at a rate of 1 ml/minute per liter of solution. The pH was monitored over the course of base addition, which was stopped at pH 8.6. The resultant uniformly black reaction mixture, which consists of finely divided protein magnetite particles, was pelleted from solution by magnetic separation. The protein magnetite pellet was twice washed with water by uniformly suspending the pellet in a quantity of water equal to the starting reaction volumes. This was followed by two washes in 20 mM phosphate buffer, pH 7.5, and finally resuspension into 20 mM phosphate buffer containing 0.1% BSA and 0.2% azide (Sigma Chemical Company), as a preservative. To insure uniform colloidal suspensions, preparations were briefly sonicated. This was accomplished by using a Heat Systems—Ultrasonic Incorporated, Farmingdale, N.Y., sonicator, Model #W-385, equipped with flow-through cell. During the process the latter was submerged in a cold bath maintained at 0° C. using a Neslab, Portsmith, N.H. cooling finger. The solution was sonicated at 20% power output, at a rate of 15 ml. per minute.

Colloidal protein magnetite solutions so prepared ranged in size from 50–90 nanometers as determined by a sub-micron particle analysis performed on a Coulter Model N4SD laser light scattering device (Coulter Electronics, Hialeah, Fla.). Solutions containing the resultant particles are stable over long periods of time, showing little or no sediment. Binding activity for the various immobilized antibodies recovered ranged from 7 to 14%. When 0.5 ml 2–30% aliquots of the colloidal protein magnetite thus produced are placed in 12×75 mm test tubes and inserted into a magnetic separation unit (Corning Medical, Medfield, Mass.) no accumulation of magnetite was observed on the sides of the tube facing the pole pieces when left in the rack for 5 minutes. As a basis of comparison, a suspension of approximately one micron diameter magnetic particles obtained from Advanced Magnetics, Cambridge, Mass. was totally cleared from solution in 40 seconds.

EXAMPLE II

Flocculation/Coagulation of Colloidal Protein Magnetite in Assay Media

Colloidal protein magnetite, prepared as described in Example 1, is an anionic colloid as evidenced by its electrophilic property, as well as its salting out sensitivity to di- and trivalent cations. To determine the effect of human serum and varying concentration of agglomerating agent on agglomerate formation, colloidal protein magnetites were prepared according to Example 1 and studied with various agents, as described below.

A. Influence of human serum on the coagulation of colloidal protein magnetite particles by Sodium Chloride (NaCl).

Forty-seven individual human serum samples and human serum pools from different sources, as well as a grossly hemolyzed serum sample were tested in a mock conversion immunossay procedure so as to evaluate the influence of variations in chemical constituents inherent in different serums on the coagulation of colloidal protein magnetite particles over a one hour period at different concentrations of sodium chloride ions.

Briefly, 100 ul serum specimens were mixed with 100 ul of the conversion buffer (0.2M TRIS, 0.8M NaCl, 0.1% BSA/N₃, pH 7.5) and 100 ul of colloidal protein magnetite in test tubes. These mixtures were left to incubate for one hour at room temperature and then all tubes were placed in a magnetic rack and allowed to stand for 3 minutes. In an actual immunoassay, the conversion buffer would also contain the labeled biospecific binding partner for the target substance. All tubes showed complete conversion to an agglomerate that could be magnetically separated. It is to be noted that the above mentioned conversion buffer was formulated such that colloidal particles would become agglomerated at the end of a one hour incubation. Therefore, for immunoassays requiring different time periods of incubation, the concentration of salt would have to be appropriately modified.

B. Effect of concentration of NaCl required for coagulation of various colloidal protein magnetite preparations.

Experiments were performed with different batches of colloidal protein magnetite using a range of sodium chloride concentrations in order to determine the optimal amount of NaCl required for coagulating the colloidal particles over a typical one hour incubation period.

The results of these experiments are presented in the following table. (Iron has a broad constant absorption spectrum over the visible range, and any wavelength may be used to measure the amount of light scattered.)

| | | | | BATCH #29043-1 | | | | | | | |
|---|---|---|---|---|---|---|---|---|---|---|---|
| NaCl (Moles/Liter) | 0 | 0.2 | 0.4 | 0.6 | 0.8 | 1.0* | 1.2 | 1.4 | 1.6 | 1.8 | 2.0 |
| Absorbance (@400 nm) | .708 | .668 | .624 | .422 | .254 | .140 | .146 | .094 | .060 | .062 | .038 |
| | | | | BATCH #29043-2 | | | | | | | |
| NaCl (Moles/Liter) | 0 | 0.2 | 0.4 | 0.6 | 0.8 | 1.0* | 1.2 | 1.4 | 1.6 | 1.8 | 2.0 |
| Absorbance (@400 nm) | .852 | .835 | .798 | .715 | .309 | .111 | .045 | .026 | .015 | .021 | .016 |
| | | | | BATCH #29043-3 | | | | | | | |
| NaCl (Moles/Liter) | 0 | 0.2 | 0.4 | 0.6 | 0.8 | 1.0* | 1.2 | 1.4 | 1.6 | 1.8 | 2.0 |
| Absorbance (@400 nm) | .929 | .849 | .837 | .531 | .231 | .080 | .016 | .013 | .009 | .005 | .006 |

The asterisks (*) denote the cutoff points.

An absorbance of ≦0.1 is seen as a clear supernatant with the naked eye after allowing a 3 minute magnetic separation and, therefore, is chosen as the cutoff point for determining the concentration of NaCl required to coagulate quantitatively the various colloidal magnetite preparations.

C. Effect on non-specific binding (NSB) of the labeled binding partner by the use of Barium Chloride ($BaCl_2$) as a coagulating agent.

In this assay, the salt is added at the end of the incubation period and this salt causes an instantaneous and quantitative coagulation of the colloidal particles into agglomerates that can be magnetically separated.

The effect on non-specific binding (NSB) of a labeled-binding partner using such a salt as a coagulant was studied as well as the effect of the concentration of the salt on non-specific binding.

Briefly, 200 ul of human serum was mixed with 100 ul of a radiolabeled binding partner and 100 ul of colloidal magnetite to which was covalently bound the other respective binding partner. In a control assay, for measuring non-specific binding, a colloidal magnetite preparation, devoid of the binding partner, was used. The mixtures were incubated for one-half hour and then various concentrations of BaCl (50 ul) were added to each tube. After separation on a magnetic rack and a wash step, the pellets were quantitated for bound label.

Initially, NSB of 2% was found using 1.5m BaCl as a coagulant. However, the results of the above experiments showed that 0.2M $BaCl_2$ is sufficient to cause quantitative coagulation and that at this concentration of $BaCl_2$, the NSB is reduced to less than 1% which is comfortably within acceptable levels for all types of immunoassays employing radio- or enzyme labels.

D. Use of second antibody as a specific flocculant.

In this method of performing an immunoassay, a second antibody is used to flocculate colloidal magnetic particles that contain the primary antibody, after the biospecific affinity reaction is complete.

Experiments were performed to compare this type of colloidal conversion with that using micron-size magnetite particles, where no conversion is necessary since such particles are permanently magnetic and much larger in size. In this way the efficacy of performing a colloidal conversion immunoassay using second antibody can be directly assessed.

Briefly, 200 ul of serum is mixed with 100 ul of 125$_I$-labeled mouse IgG (~30,000 cpm), 100 ul of mouse IgG (0–250 ng.) and 100 ul of colloidal magnetite covalently bound to goat anti-mouse IgG(Fc specific) antibodies. After half an hour incubation at room temperature, a 100 ul solution of rabbit anti-goat antibodies (2 ug) is added to each tube, and immediately these antibodies become bound to the goat antibodies on the colloidal particles and hence form, by flocculation, large agglomerates that can be magnetically separated. Then, after separation on a magnetic rack and a wash step, the pellets are quantitated for bound label. In the (positive) control experiment, 200 ul of serum is mixed with 100 ul of 125$_I$-labeled mouse IgG (~30,000 cpm), 100 ul of mouse IgG (0–250 ng.) and 100 ul of micron-size magnetite containing covalently bound goat anti-mouse IgG(Fc specific) antibodies. After a half hour incubation at room temperature, the magnetite is separated on a magnetic rack, washed, and the pellets quantitated for bound label.

The results of these experiments are shown in tabulated form below.

| (A) COLLOIDAL MAGNETITE CONVERSION ASSAY RESULTS | | | | | | |
|---|---|---|---|---|---|---|
| ng. Cold IgG added | 0 | 50 | 100 | 150 | 200 | 250 |
| % Bound Counts | 67 | 52 | 44 | 37 | 32 | 28 |
| (B) MICRON-SIZE MAGNETITE | | | | | | |

-continued

| CONVERSION ASSAY RESULTS | | | | | | |
|---|---|---|---|---|---|---|
| ng. Cold IgG added | 0 | 50 | 100 | 150 | 200 | 250 |
| % Bound Counts | 61 | 49 | 42 | 38 | 30 | 25 |

As can be seen from this experiment, the colloidal conversion assay gives an almost identical inhibition curve to that of the assay done with micron-size magnetite. The slightly higher binding at '0' ng. cold mouse IgG added is to be expected because of a larger surface area available for reaction. Therefore, flocculation using a second antibody is a practicable and most feasible format for performing immunoassays of both the competitive and sandwich type.

EXAMPLE III

Coagulation/Flocculation Using a Second Colloid

Latex reagent (latex particles coated with human IgG) was obtained from Wampole Laboratories, Cranbury, N.J. This material is normally used to test for rheumatoid factor.

Aliquots of latex reagent, containing 50, 25 and 10 ul, respectively, were added in triplicate to 0.5 mls of 0.1% BSA in 20 mM phosphate buffer pH 7.5 in 12×75 mm glass tubes and vortexed. For each latex concentration, BSA colloidal magnetite, prepared according to Example 1, was added as follows: 50 ul to sample 1, 100 ul to sample 2, and 200 ul to sample 3. Samples were vortexed and incubated at room temperature for 30 minutes during which time no signs of settling were visible. When samples were placed in the Corning magnetic separator for 15 minutes, all pulled clear of latex as judge visually, and as determined by removing the supernatant, resuspending the magnetic pellet in buffer and comparing the turbidity of the resuspended material with the starting mixture. The color of the supernatents were varying shades of amber (identical to diluted colloidal magnetite), in proportion to the increasing concentration of colloidal magnetite employed. This indicates that for this system the magnetic colloid was in excess. Furthermore, the resuspended pellets were colored in proportion to the concentration of colloidal magnetite added. Washed pellets could be repeatedly resuspended and magnetically separated indicating a stable colloid-colloid interaction. Over a 6-8 hour period resuspended pellets showed no signs of settling. Identical results for the above experiments were obtained with a colloidal protein magnetite which contained the rabbit IgG described in Ex. 1, rather than BSA. It should be further noted that this example should have application to cellular systems for clinical or industrial uses.

Coagulation/flocculation of colloidal protein can also be obtained with Clq. Human Clq was isolated as described by Liberti, et al., *J. Immunological Methods*, 40:243–45 (1981). An aliquot of Clq was inactivated (Liberti, unpublished result), by 10 minute treatment with 5 mM chloramine T (Fisher, King of Prussia, Pa.). This inactivated sample could not agglutinate latex reagent. When samples of both the active and inactivated Clq preparations were mixed with 100 ul samples of colloidal protein magnetite (BSA, rabbit IgG, monoclonal anti-HCG or rabbit anti-fluorescein) diluted in 0.1% BSA, 20 mM phosphate buffer, pH 7.5, it was found that 40 ug of Clq resulted in a magnetic colloid-colloid complex which could be separated via the magnetic rack and which had no signs of magnetite in the supernatants. Such complexes could be water or buffer washed and repeatedly magnetically separated. Poly lysine or poly lysine-containing polymers could also be used as the agglomerating agent in place of Clq.

EXAMPLE IV

Two Site Sandwich Assays Via Colloidal Conversion

Colloidal protein magnetite preparations were prepared as described in Example 1, comprising goat anti-mouse IgG (Fc specific), rabbit anti-fluorescein and mouse monoclonal anti-HCG. (Fab)$_2$ of a second monoclonal was prepared by pepsin digestion followed by absorption on goat anti-mouse Fc sepharose prepared by standard activation and coupling techniques. This (Fab)$_2$ and its parent monoclonal were labeled with 5 u Ci/ug $^{125}$I, by the Iodogen method of Fraker et al., *Biochem. Biophys. Res. Comm.*, 80:849 (1978). HCG (Sigma, St. Louis, Mo.) standards were prepared at 0, 5, 25, 54, and 361 mIU/ml in HCG free human serum (Scantibodies, Foster City, Calif.). Anti HCG monoclonals were fluoresceinated to 6-7 moles/mole IgG as described by Haaijam, "Immunohistochemistry," ed. Cuello pp. 47-86, IBRO Handbook Series, Wiley, Chichester, (1983). Assays were performed by mixing 200 ul of standard with 100 ul of 100,000 cpm of the appropriate labeled reagent and second monoclonal and 100 ul of the appropriate colloidal magnetite as follows:

a. $^{125}$I anti-HCG (Fab)$_2$, anti-HCG (second monoclonal) and colloidal anti-mouse Fc magnetite.

b. $^{125}$I anti-HCG, fluorescein labeled anti-HCG (second monoclonal) and colloidal anti-fluorescein magnetite.

c. $^{125}$I anti-HCG and colloidal anti-HCG (second monoclonal) magnetite, and d. A repeat of "c" except that $^{125}$I anti-HCG (Fab)$_2$ was substituted as the labeled reagent. After a 30 minute room temperature incubation, 150 ul of 0.5m BaCl$_2$ in 1.3M NaCl, 20 mM phosphate buffer, pH 7.5 was added to each sample, mixed and then incubated for 5 minutes and placed in the magnetic separator rack for 30 minutes, after which clear supernatant was removed. Magnetic pellets were washed once with 0.3M NaCl containing 0.05M BaCl$_2$, magnetically separated as above and counted in a Nuclear Chicago gamma spectrometer (Chicago, Ill.). The results obtained are tabulated below, with column head letters corresponding to the mixtures described above.

| HCG mIU | a. Anti Fc Magnet. | b. Anti Flur. Magnet. | c. Anti HCG | d. Magnet. |
|---|---|---|---|---|
| 0 | 952 | 932 | 870 | 630 |
| 5 | 1304 | 1351 | 1302 | 1016 |
| 25 | 2095 | 2092 | 2103 | 1801 |
| 54 | 3268 | 3316 | 3302 | 2420 |
| 361 | 7094 | 7160 | 7114 | 6912 |

As can be seen, good quantitation was obtained. Further, the use of (Fab)$_2$ gives somewhat lower non-specific binding, which is consistent with reports by others. See, for example, Beck, et al., *Biochem. J.*, 145:607 (1975); Kato et al., *J. Immunol.*, 116:1554 (1976); and Yoshitake et al., *Scand J. Immunol.*, 10:81 (1979). Experiments using a second colloidal protein magnetite as a flocculating agent, having binding affinity for a determinant on the first colloid protein magnetite yielded equally good results. This was done using colloidal goat anti-rabbit IgG magnetite directed to the rabbit IgG of colloidal anti-fluorescene magnetite (the latter being of rabbit origin as noted above) of column "b" above.

EXAMPLE V

Detection of Analyte by Conversion of Colloid to Magnetic Flocculate

Because colloidal protein magnetite can be flocculated to become susceptible to separation from solution by an externally applied magnetic field, the presence of a target substance in a specimen can be detected simply by the ability of a magnetic field to clear a solution of colloidal magnetite bearing an appropriate receptor, i.e. by this same phenomenon. To demonstrate this, colloidal goat anti-mouse IgG magnetite was prepared as described in Example 1. Test samples (100 ul) containing 1 to 200 ug of mouse IgG were incubated with 100 ul dilutions (1/0 to 1/20) of the colloidal solution for 30 minutes in 12×75 mm test tubes and then placed in a Corning Magnetic Separator Rack. Control samples containing no mouse IgG or non-specific colloidal protein magnetite remained in solution when subjected to the magnetic field. On the other hand, samples containing as little as 10 ug mouse IgG resulted in magnetic pellets appearing adjacent to the pole pieces and a clearing of supernatents. Greater sensitivity would likely be achievable by increasing ionic strength of the system, through addition of specific ions or appropriate miscible solvents.

While our method for manipulating magnetic colloids to facilitate their separation from solution has been described herein in terms of certain preferred embodiments, various other embodiments will be apparent to those skilled in the art. For example, metals other than iron may be used in preparing the colloidal magnetic particles. Furthermore, a wide range of protein coatings, in addition to those specifically mentioned above, may be provided on the magnetic particles. The invention is, therefore, not limited to the embodiments actually described, but is capable of variation and modification without departing from the spirit and scope of the appended claims.

What is claimed is:

1. A method for magnetically separating a target substance from a test medium suspected of containing said substance said target substance being one member of a specific binding pair, said method comprising:
    adding to said test medium agglomerable and resuspendable colloidal particles, said particles when unagglomerated, being capable of stable suspension in said test medium;
    forming a magnetic agglomerate comprising said colloidal particles and the product of a biospecific affinity reaction between said target substance and the other member of said specific binding pair, at least one member of said specific binding pair comprising a bioactive protein, said protein, or a bioactive protein capable of binding specifically to at least one member of said specific binding pair, being attached to said colloidal particles; and
    separating said agglomerate from said test medium the suspension stability of said particles being substantially undisturbed when subjected to an externally applied magnetic field.

2. A method as claimed in claim 1, wherein the colloidal particles added to said test medium comprise said protein capable of binding specifically to at least one member of said specific binding pair.

3. A method as claimed in claim 2, wherein the colloidal particles added to said test medium comprise a protein capable of binding to said bioactive protein member of said binding pair.

4. A method as claimed in claim 2, wherein said agglomerate is formed by binding of said bioactive protein member of said binding pair to said target pair.

5. A method as claimed in claim 2, wherein an additional binding substance capable of binding specifically to said target substance is contacted with said test medium.

6. A method as claimed in claim 5, wherein said agglomerate is formed by binding of said additional binding substance to said target substance.

7. A method as claimed in claim 5, which includes contacting said test medium with at least one agglomerating agent to promote forming said agglomerate.

8. A method as claimed in claim 7, wherein said agglomerate is formed by contacting said test medium with a non-specific agglomerating agent selected from the group consisting of an alkali metal salt, an alkaline earth metal salt, a colloidal material, ammonium sulfate, an agglomerating solvent, or polyethylene glycol.

9. A method as claimed in claim 7, wherein said agglomerating agent contacted with said test medium comprises magnetic material and is incorporated into said agglomerate.

10. A method as claimed in claim 9, wherein said agglomerating agent contacted with said test medium comprises particulate magnetite having a particle size from about 0.01 to about 0.20 microns.

11. A method as claimed in claim 9, wherein said agglomerating agent contacted with said test medium comprises colloidal material.

12. A method as claimed in claim 7, wherein a specific agglomerating agent is added to said test medium.

13. A method as claimed in claim 2, wherein said agglomerate is formed by contacting said test medium with at least one agglomerating agent.

14. A method as claimed in claim 13, wherein said agglomerate is formed by contacting said test medium with a non-specific agglomerating agent selected from the group consisting of an alkali metal salt, an alkaline earth metal salt, a colloidal material, ammonium sulfate, an agglomerating solvent, or polyethylene glycol.

15. A method as claimed in claim 13, wherein said agglomerating agent contacted with said test medium comprises magnetic material and is incorporated into said agglomerate.

16. A method as claimed in claim 15, wherein said agglomerating agent contacted with said test medium comprises particulate magnetite having a particle size from about 0.01 to about 0.20 microns.

17. A method as claimed in claim 15, wherein said agglomerating agent contacted with said test medium comprises colloidal material.

18. A method as claimed in claim 1, wherein a magnetic field is applied to separate said agglomerate from said test medium.

19. A method as claimed in claim 18, wherein colloidal particles comprising magnetic material are added to said test medium.

20. A method as claimed in claim 19, wherein colloidal particle comprising magnetite and having a particle size from about 0.01 to about 0.20 microns are added to said test medium.

21. A method as claimed in claim 19, wherein colloidal particles added to said test medium are attached to a member of said binding pair comprising said bioactive protein.

22. A method as claimed in claim 21, wherein said agglomerate is formed by binding of said bioactive protein member of said binding pair to said target substance.

23. A method as claimed in claim 21, wherein an additional binding substance capable of binding specifically to said target substance is contacted with said test medium.

24. A method as claimed in claim 23, wherein said agglomerate is formed by binding of said additional binding substance to said target substance.

25. A method as claimed in claim 23 which includes adding to said test medium at least one agglomerating agent to promote forming said agglomerate.

26. A method as claimed in claim 25 wherein there is added to said test medium a non-specific agglomerating agent selected from the group consisting of an alkali metal salt, an alkaline earth metal salt, a colloidal material, ammonium sulfate, a non-solvent for said agglomerate or polyethylene glycol.

27. A method as claimed in claim 25, wherein said non-specific agglomerating agent added to said test medium comprises magnetic material and is incorporated into said agglomerate.

28. A method as claimed in claim 27, wherein said non-specific agglomerating agent contacted with said test medium comprises particulate magnetite having a particle size from about 0.01 to about 0.20 microns.

29. A method as claimed in claim 27, wherein said non-specific agglomerating agent contacted with said test medium comprises colloidal material.

30. A method as claimed in claim 25, wherein a specific agglomerate agent is added to said test medium.

31. A method as claimed in claim 1, wherein colloidal particles added to said test medium comprise said member of said binding pair comprising said bioactive protein.

32. A method as claimed in claim 31, wherein said agglomerate is formed by contacting said test medium with at lest one agglomerating agent.

33. A method as claimed in claim 32, wherein said agglomerate is formed by contacting said test medium with a non-specific agglomerating agent selected from the group consisting of an alkali metal salt, an alkaline earth metal salt, a colloidal material, ammonium sulfate, a non-solvent for said agglomerate or polyethylene glycol.

34. A method as claimed in claim 32, wherein a specific agglomerating agent is added to said test medium.

35. A method as claimed in claim 32, wherein said agglomerating agent contacted with said test medium comprises magnetic material and is incorporated into said agglomerate.

36. A method as claimed in claim 35, wherein said agglomerating agent contacted with said test medium comprises particulate magnetite having a particle size from about 0.01 to about 0.20 microns.

37. A method as claimed in claim 35, wherein said agglomerating agent contacted with said test medium comprises colloidal material.

38. A method for magnetically separating a substance, selected from the group consisting of antigens, antibodies, biological factors, cells, cell components and, viruses, from a biological fluid suspected of containing said substance, each said substance having at least one characteristic determinant associated therewith, said process comprising:
 contacting said biological fluid with agglomerable and resuspendable colloidal magnetic particles bearing a proteinaceous receptor capable of binding specifically to a determinant of said substance, said particles, when unagglomerated, being capable of stable suspension in said biological fluid, the suspension stability of said particles being substantially undisturbed when subjected to an externally applied magnetic field;
 subjecting said biological fluid to conditions causing binding between said receptor and said determinant;
 forming a magnetic agglomerate comprising said particles and any of said substance present in said biological fluid; and
 applying a magnetic field to separate said magnetic agglomerate from said biological fluid.

39. A method as claimed in claim 38, wherein said agglomerate is formed as a result of binding between said receptor and said determinant.

40. A method as claimed in claim 38, wherein said agglomerate is formed by adding to said biological fluid at least one non-specific agglomerating agent.

41. A method for magnetically separating a substance, selected from the group consisting of antigens, antibodies, biological factors, cells, cell components and, viruses, from a biological fluid suspected of containing said substance and determining the presence or quantity of said substance in said biological fluid, each said substance having at least one characteristic determinant associated therewith, said process comprising:
 adding to said biological fluid agglomerable and resuspendable colloidal magnetic particles bearing a proteinaceous receptor capable of binding specifically to a determinant of said substance, and a labeled binding substance having specific binding affinity for the substance to be separated and determined, said particles, when unagglomerated, being capable of stable suspension in said biological fluid, the suspension stability of said particles being substantially undisturbed when subjected to an externally applied magnetic field;
 subjecting said biological fluid to conditions causing binding between said receptor and said determinant;
 contacting said biological fluid with an agglomerating agent, thereby to yield an agglomerate comprising said colloidal magnetic particles bound to said substance;
 applying a magnetic field to separate said biological fluid into a portion comprising said magnetic agglomerate and a portion substantially free of said magnetic agglomerate; and
 detecting or quantitating the labeled binding substance in one of said portions as a measure of the presence of quantity of said substance in said biological fluid.

42. A method as claimed in claim 41, wherein said biological fluid is contacted with at least one non-specific agglomerating agent.

43. A method as claimed in claim 41, wherein agglomerable and resuspendable colloidal magnetic particles comprising a specific binding moiety having binding affinity for said receptor are added to said biological fluid.

44. A method for magnetically separating a substance, selected from the group consisting of antigens, antibodies, biological factors, cells, cell components and, viruses, from a biological fluid suspected of containing said substance, each said substance having at least one characteristic determinant associated therewith, said process comprising:
  adding to said biological fluid agglomerable and resuspendable colloidal magnetic particles bearing a proteinaceous receptor capable of binding specifically to a determinant of said substance, said particles, when unagglomerated, being capable of stable suspension in said biological fluid, the suspension stability of said particle being substantially undisturbed when subjected to an externally applied magnetic field;
  subjecting said biological fluid to conditions causing binding between said receptor and said determinant;
  adding at least one agglomerating agent to said biological fluid to form a magnetic agglomerate comprising said colloidal magnetic particles bound to said substance; and
  applying a magnetic field to separate said magnetic agglomerate from said biological fluid.

45. A method as claimed in claim 44, wherein said agglomerate is formed by adding to said biological fluid at least one non-specific agglomerating agent.

46. A method for magnetically separating a substance, selected from the group consisting of antigens, antibodies, biological factors, cells, cell components and viruses, from a biological fluid suspected of containing said substance, each said substance having at least one characteristic determinant associated therewith, said process comprising:
  adding to said biological fluid a receptor capable of binding specifically to a determinant of said substance and having one member of a specific binding pair associated therewith;
  subjecting said biological fluid to conditions causing binding between said receptor and said determinant to yield an agglomerate comprising said receptor bound to said substance;
  contacting said biological fluid with agglomerable and resuspendable protein-bearing colloidal magnetic particles said protein comprising the other member of said specific binding pair, said particles, when unagglomerated, being capable of stable suspension in said biological fluid, the suspension stability of said particles being substantially undisturbed when subject to an externally applied magnetic field, said contacting occurring under conditions causing binding between said members, thereby to render said agglomerate magnetic; and
  applying a magnetic field to separate said magnetic agglomerate from said biological fluid.

47. A method as claimed in claim 46, wherein said one member of said specific binding pair is an antigen and said other member of said pair is an antibody which immunospecifically interacts with said antigen.

48. A method as claimed in claim 46, wherein said biological fluid is contacted with at least one non-specific agglomerating agent.

49. A method for magnetically separating a substance, selected from the group consisting of antigens, antibodies, biological factors, cells, cell components and viruses, from a biological fluid suspected of containing said substance, and determining the presence or quantity of said substance in said biological fluid, each substance having at least two characteristic determinants associated therewith, said process comprising:
  adding to said biological fluid a receptor capable of binding specifically to a first of said determinants and having one member of a specific binding pair associated therewith, and a labeled binding substance having specific binding affinity for a second of said determinants;
  subjecting said biological fluid to conditions causing binding between said receptor and said first determinant and between said labeled binding substance and said second determinant;
  contacting said biological fluid with agglomerable and resuspendable, protein-bearing colloidal magnetic particles said protein comprising the other member of said specific binding pair, said particles, when unagglomerated, being capable of stable suspension in said biological fluid, the suspension stability of said particles being substantially undisturbed when subjected to an externally applied magnetic field, said contacting occurring under conditions causing binding between said members;
  adding to said biological fluid an agglomerating agent thereby to yield a magnetic agglomerate comprising said colloidal particles bound to said substance;
  applying a magnetic field to separate said biological fluid into a portion comprising said magnetic agglomerate and a portion substantially free of said magnetic agglomerate; and
  detecting or quantitating the labeled binding substance in one of said portions as a measure of the presence or quantity of said substance in said biological fluid.

50. A method as claimed in claim 49, wherein agglomerable and resuspendable colloidal magnetic particles comprising a specific binding moiety having binding affinity for said receptor are added to said biological fluid.

51. A method as claimed in claim 49, wherein said one member of said specific binding pair is an antigen and said other member of said pair is an antibody which immunospecifically interacts with said antigen.

52. A method as claimed in claim 49, wherein said biological fluid is contacted with at least one non-specific agglomerating agent.

53. A method for magnetically separating a substance, selected from the group consisting of antigens, antibodies, biological factors, cells, cell components and viruses, from a biological fluid suspected of containing said substance, each substance having at lest one characteristic determinant associated therewith, said process comprising:
  adding to said biological fluid a receptor capable of binding specifically to a determinant of said substance and having one member of a specific binding pair associated therewith;
  subjecting said biological fluid to conditions causing binding between said receptor and said determinant;
  contacting said biological fluid with agglomerable and resuspendable, protein-bearing colloidal particles said protein comprising the other member of said specific binding pair, said particles, when unagglomerated, being capable of stable suspension in said biological fluid, the suspension stability of said particles being substantially undisturbed when subjected to an externally applied magnetic field, said contacting occurring under conditions causing binding between said members;

contacting said biological fluid with at least one agglomerating agent, thereby to form an agglomerate comprising said magnetic colloidal particles bound to said substance; and applying a magnetic field to separate said magnetic agglomerate from said biological fluid.

54. A method as claimed in claim 53, wherein said agglomerate is formed by contacting said biological fluid with a non-specific agglomerating agent.

55. A method as claimed in claim 53, wherein said non-specific agglomerating agent added to said biological fluid comprises colloidal magnetic material.

56. A method for determining the presence of a substance in a biological fluid suspected of containing said substance, in excess of a predetermined level, said substance being selected from the group of antigens, antibodies, biological factors, cells, cell components and, viruses, each said substance having at least one characteristic determinant associated therewith, said process comprising:

contacting said biological fluid with agglomerable and resuspendable colloidal magnetic particles bearing a proteinaceous receptor capable of binding specifically to a determinant of said substance so as to form an agglomerate, said particles, when unagglomerated, being capable of stable suspension in said biological fluid, the suspension stability of said particles being substantially undisturbed when subjected to an externally applied magnetic field, the amount of said particles being sufficient that any said agglomerate so formed is separable from said biological fluid under the influence of an externally-applied magnetic field when the amount of said substance in said biological fluid exceeds said predetermined level;

subjecting said biological fluid to conditions causing binding between said receptor and said determinant;

applying an external magnetic field to said biological fluid; and determining the occurrence of separated agglomerate as an indication of the presence of said substance in excess of said predetermined amount.

57. A method as claimed in claim 56, wherein the occurrence of separated agglomerate is visually determined.

58. A method for determining the presence of a protein-containing substance in a biological fluid suspected of containing said substance, in excess of a pre-determined level, said substance being selected from the group of antigens, antibodies, biological factors, cells, cell components and, viruses, each said substance having at least one characteristic monovalent determinant associated therewith, said process comprising:

contacting said biological fluid with a receptor capable of binding specifically to said determinant, and with agglomerable and resuspendable colloidal magnetic particles bearing said protein-containing substance in a form providing a plurality of said determinants associated with said particles, said particles, when unagglomerated, being capable of stable suspension in said biological fluid, the suspension stability of said particles being substantially undisturbed when subjected to an externally applied magnetic field, the relative amounts of said receptor and said particles being sufficient to form an agglomerate which is magnetically separable from said biological fluid under the influence of an externally-applied magnetic field when the amount of said substance in said biological fluid is below said pre-determined level;

subjecting said biological fluid to conditions causing binding between said receptor and said determinants;

applying an external magnetic field to said biological fluid; and determining the occurrence of separated agglomerate as an indication of the presence of said substance in excess of said predetermined level.

59. A method as claimed in claim 58, wherein the occurrence of separated agglomerate is visually determined.

60. A method as claimed in claim 58, wherein determining the occurrence of separated agglomerate is facilitated by labeling said receptor with a detectable label selected from the group consisting of an enzyme, a radioisotope or a fluorescent or phosphorescent substance.

* * * * *

UNITED STATES PATENT AND TRADEMARK OFFICE
CERTIFICATE OF CORRECTION

PATENT NO. : 5,108,933
DATED : April 28, 1992
INVENTOR(S) : Paul A. Liberti and Dhanesh I. Gohel It is certified that error appears in the above-identified patent and that said Letters Patent is hereby corrected as shown below:

Column 20, line 9, change "pair" to --substance--.

Column 21, line 46, change "lest" to --least--.

Column 22, line 2, delete "," before "viruses".

Column 22, line 33, delete "," before "viruses".

Column 23, line 6, delete "," before "viruses".

Column 23, line 53, change "subject" to --subjected--.

Column 24, line 53, change "lest" to --least--.

Signed and Sealed this

Twenty-ninth Day of March, 1994

*Attest:*

BRUCE LEHMAN

*Attesting Officer*  Commissioner of Patents and Trademarks